United States Patent [19]

van Andel

[11] Patent Number: Plant 6,033

[45] Date of Patent: Oct. 6, 1987

[54] ALSTROEMERIA NAMED STALAN

[75] Inventor: Jacob van Andel, Aalsmeer, Netherlands

[73] Assignee: Van Staaveren B.V., Aalsmeer, Netherlands

[21] Appl. No.: 805,717

[22] Filed: Dec. 6, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new variety of Alstroemeria plant characterized by its year around production of medium sized flowers having a generally Magenta Rose coloration for its relatively large flower petals which contrasts severely with the Primrose Yellow and Sulphur Yellow coloration of the two larger ones of the upper petals which are heavily streaked with longitudinally extending Brown pencil stripes, the plant itself being of a more-or-less medium size with a strong, vigorous and upright growth habit and the flowers having a good lasting quality both on the plant and as cut flowers.

1 Drawing Figure

BACKGROUND OF THE NEW PLANT

This new variety of Alstroemeria plant originated as a seedling resulting from my crossing of selected stock plants individually identified in my records and maintained for breeding purposes, this crossing being done in the course of breeding efforts carried on by me since 1981 with the purpose of producing new types of alstroemeria plants. This particular seedling was selected because of the very unusual combination of light and dark Magenta colors which are sharply contrasted with the very light Yellow coloring of the larger of the two uppermost petals which are very heavily streaked with relatively long longitudinally extending pencil stripes. Propagation of this new seedling was done by me and under my direction at Aalsmeer, The Netherlands, by root division and such propagation was carried on through several generations at Aalsmeer, which demonstrated that the plants of this new variety would hold their novel characteristics from generation to generation and that these characteristics appeared to be firmly fixed.

DESCRIPTION OF THE DRAWING

This new variety of Alstroemeria plant is illustrated by the accompanying photographic drawing which, in full color, shows the flower form and coloration of the blooms of this plant, the color rendition being as nearly true to the specified colors as is possible to obtain by conventional photographic procedures.

DESCRIPTION OF THE NEW PLANT

The following is a detailed description of my new alstroemeria plant with color designations according to The R.H.S. Colour Chart of The Royal Horticultural Society of London, England.

THE PLANT

Origin: Seedling.

Parentage:

*Seed parent.*—Breeding Stock Plant No. 7326-1 (unpatented).

*Pollen parent.*—Breeding Stock Plant No. 0333-1 (unpatented).

Classification:

*Botanic.*—Alstroemeria Hybrid.

*Commercial.*—Alstroemeria.

Form: Erect bush.

Height: About 140 cm.

Growth: Vigorous, strong and upright.

Root stock: Tuberous.

Foliage:

*Quantity.*—Medium.

*Number of leaves.*—Various, depending on season.

*Size of leaf.*—Various, depending on season.

*Shape.*—Elliptic with entire margins.

*Texture.*—Leathery.

*Color.*—Upper side — Middle Green. Under side — Middle Green.

Rhizomes:

*Color.*—White.

*Size.*—Various, depending on season.

THE BUD

Form: Pear shaped.

Size: Medium.

*Diameter.*—About 25 mm.

*Length.*—About 45 mm.

Peduncle:

*Length.*—About 20 mm.

*Color.*—Medium Green.

*Character.*—The peduncle extends upwardly at about an angle of 30° from the main stem.

THE FLOWER

Blooming habit: Continuous the year around.

Flower size.—Medium.

*Diameter.*—About 50 mm.

*Depth.*—About 55 mm.

Borne: Singly.

Shape: Funnel-like with petal tips curling outwardly when bloom matures.

Petalage:

*Number of petals.*—Six.

*Arrangement.*—Two concentric circles of three petals each.

*Form.*—Obovate with obcordate apex.

*Texture.*—Leathery.

*Appearance.*—Shiny.

*Color.*—Lower petals — Upper side, 64D fading to 65B for a wide margin. Lower side, 64C/D. Upper petals — Body, 64D with center portion of 4D fading to 6 C toward the tip end which is 64D. Reverse side, 64D+4D.

Persistence: The flowers hang on and dry.

Lasting quality:

*On the plant.*—15 days.

*As a cut flower.*—About 10 days.

REPRODUCTIVE ORGANS

Stamens:

Anthers:

*Number.*—Six.

*Arrangement.*—One opposite each petal.

Filaments:

*Color.*—Purple/Pink.

Pollen:

*Color.*—Grey Green.

Pistils:

*Number.*—One

*Color.*—Purple Red.

Stigma:

*Color.*—Purple Red.

THE FRUIT

Fertility: The fruit is fertile.

Shape: Capsular.

Color at maturity: Light Brown.

I claim:

1. A new and distinct variety of Alstroemeria plant, substantially as herein shown and described, particularly characterized by its generally light Magenta Rose coloration of the lower petals of the flower and the contrasting light Yellow coloration of the uppermost petals which are heavily striped from base to tip.

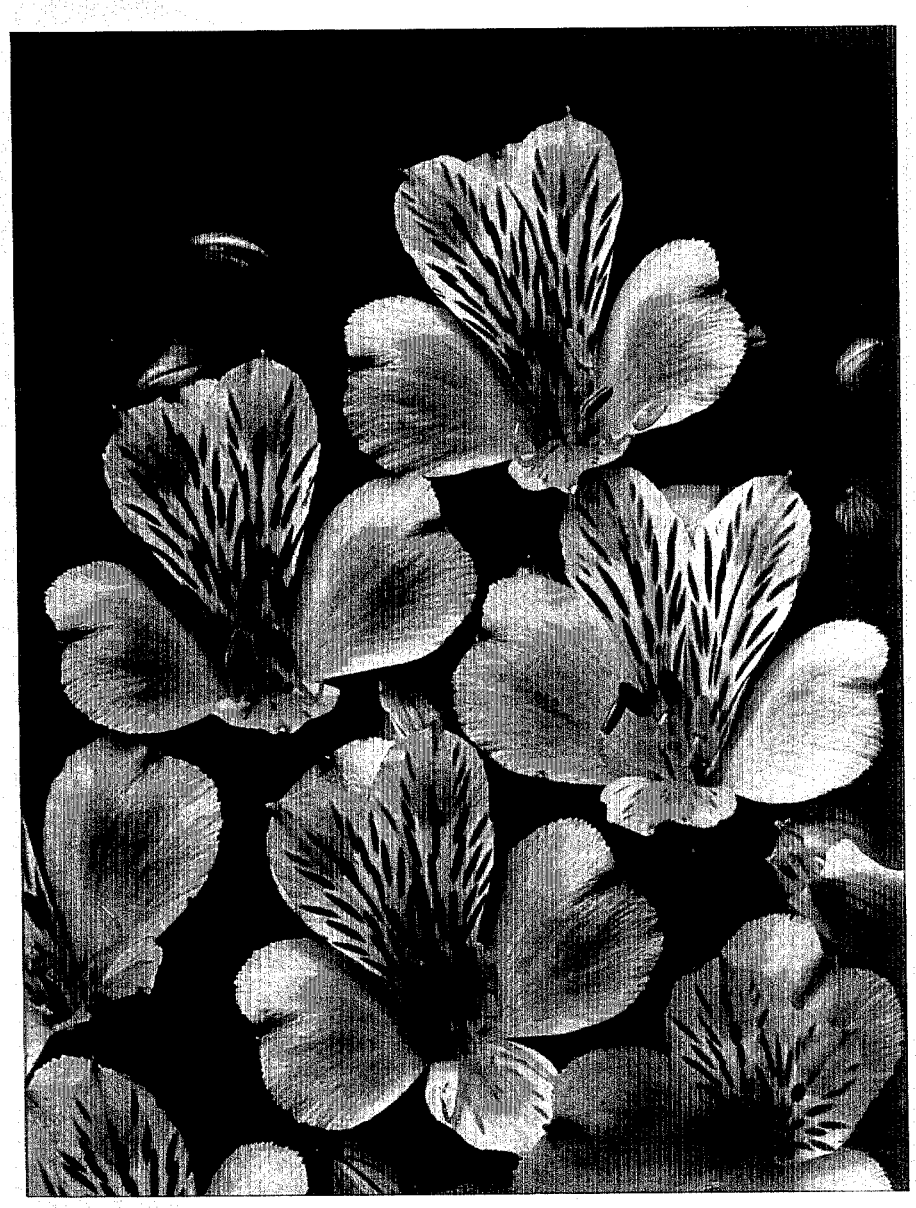

* * * * *